United States Patent
Konishi et al.

(10) Patent No.: US 10,538,878 B2
(45) Date of Patent: Jan. 21, 2020

(54) METHOD FOR RECOVERING PULP FIBERS FROM USED ABSORBENT ARTICLE

(71) Applicant: UNICHARM CORPORATION, Ehime (JP)

(72) Inventors: Takayoshi Konishi, Kagawa (JP); Toshio Hiraoka, Kagawa (JP); Koichi Yamaki, Kagawa (JP); Noritomo Kameda, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 16/322,109

(22) PCT Filed: Jun. 9, 2017

(86) PCT No.: PCT/JP2017/021539
§ 371 (c)(1),
(2) Date: Jan. 31, 2019

(87) PCT Pub. No.: WO2018/025499
PCT Pub. Date: Feb. 8, 2018

(65) Prior Publication Data
US 2019/0186074 A1   Jun. 20, 2019

(30) Foreign Application Priority Data
Aug. 5, 2016   (JP) .................................. 2016-154964

(51) Int. Cl.
| | |
|---|---|
| *D21C 5/02* | (2006.01) |
| *A61L 11/00* | (2006.01) |
| *B09B 3/00* | (2006.01) |
| *A61L 2/18* | (2006.01) |
| *B29B 17/02* | (2006.01) |
| *D21B 1/10* | (2006.01) |
| *B29L 31/48* | (2006.01) |

(52) U.S. Cl.
CPC .............. *D21C 5/022* (2013.01); *A61L 2/183* (2013.01); *A61L 11/00* (2013.01); *B09B 3/00* (2013.01); *B29B 17/02* (2013.01); *D21B 1/10* (2013.01); *B29B 2017/0224* (2013.01); *B29L 2031/4878* (2013.01)

(58) Field of Classification Search
None
See application file for complete search history.

(56) References Cited

U.S. PATENT DOCUMENTS

| | | | |
|---|---|---|---|
| 2008/0167634 A1* | 7/2008 | Kouta | ............... A61F 13/53409 |
| | | | 604/367 |
| 2015/0291762 A1 | 10/2015 | Watanabe et al. | |
| 2016/0237617 A1* | 8/2016 | Yamaguchi | ............... D21C 5/02 |
| 2017/0107667 A1 | 4/2017 | Konishi et al. | |

FOREIGN PATENT DOCUMENTS

| | | |
|---|---|---|
| EP | 3238840 A1 | 11/2017 |
| JP | H4-317785 A | 11/1992 |
| JP | 2003-39023 A | 2/2003 |
| JP | 2003-225645 A | 8/2003 |
| JP | 2010-84031 A | 4/2010 |
| JP | 2012-66156 A | 4/2012 |
| JP | 2014-217835 A | 11/2014 |
| JP | 2016-123973 A | 7/2016 |
| WO | 2014/007105 A1 | 1/2014 |
| WO | 2015/190140 A1 | 12/2015 |
| WO | 2016/103985 A1 | 6/2016 |

* cited by examiner

*Primary Examiner* — Jacob T Minskey
(74) *Attorney, Agent, or Firm* — Hauptman Ham, LLP

(57) ABSTRACT

A method is provided for recovering pulp fibers having little damage from a used absorbent article which includes a water permeable front sheet, a water impermeable back sheet and an absorbent body that contains pulp fibers and a superabsorbent polymer. At least one opening with a circle equivalent diameter of 5-45 mm, or 10-45 mm cut, is made in the front sheet and/or the back sheet of the used absorbent article, which is then agitated in an organic acid aqueous solution with a pH of less than or equal to 2.5, and the superabsorbent polymer is deactivated and the pulp fibers and superabsorbent polymer are discharged from the used absorbent article through the opening or cut.

9 Claims, No Drawings

METHOD FOR RECOVERING PULP FIBERS FROM USED ABSORBENT ARTICLE

RELATED APPLICATIONS

The present application is an National Phase of International Application Number PCT/JP2017/021539, filed on Jun. 9, 2017, and claims priority of Japanese Application Number 2016-154964, filed on Aug. 5, 2016.

FIELD

The present invention relates to a method for recovering pulp fibers from a used absorbent article. More specifically, the invention relates to a method for recovering pulp fibers from a used absorbent article that includes a water-permeable front sheet, a water-impermeable back sheet and an absorbent body that contains pulp fibers and a superabsorbent polymer, with minimal damage.

BACKGROUND

It has been attempted to recycle used absorbent articles such as disposable paper diapers. For recycling of used absorbent articles, it is common to disintegrate the used absorbent articles in water, separating them into the constituent components of the absorbent articles, which are then recovered. However, the superabsorbent polymers that are included in absorbent articles absorb moisture and increase in mass, while also gelling and losing their flow property, causing the throughput capacity of the treatment apparatus to be reduced.

In this regard, Japanese Unexamined Patent Publication No. 2010-84031 proposes a method of treating used paper diapers wherein lime, a hypochlorite and used paper diapers are loaded into a treatment tank and stirred for a prescribed period while supplying water in the minimum amount necessary for stirring in the treatment tank, the liquid in the treatment tank is discharged out of the treatment tank while dewatering, and the discharged waste water is recovered, subjected to water quality treatment and discarded.

CITATION LIST

Patent Literature

[PTL 1] Japanese Unexamined Patent Publication No. 2010-84031

SUMMARY

Technical Problem

In Japanese Unexamined Patent Publication No. 2010-84031, however, since lime is loaded in an amount sufficient for inactivation of the superabsorbent polymer, and a hypochlorite is used as a disinfectant (microbicide), the lime produces a highly alkaline environment inside the treatment tank, and this not only causes degradation of the pulp fibers, but due to the presence of a large amount of superabsorbent polymer that has been crosslinked and dewatered by calcium ions in the lime, as well as undissolved lime, the ash content in the pulp fibers recovered by the treatment is extremely high, resulting in reduced performance and quality. Furthermore, the use of a hypochlorite raises concerns regarding effects on the environment.

Solution to Problem

The present inventors have focused on these problems of the prior art, and have completed this invention upon finding that it is possible to recover pulp fibers with minimal damage by forming open holes in a used absorbent article, such as a used paper diaper, to allow the interior pulp fibers and superabsorbent polymer to leak out by the flow of washing water, thus separating them while maintaining the form of the used absorbent article, and then using an organic acid, which has a high washing effect and produces minimal damage to pulp fibers, as washing water at a pH that allows inactivation of the superabsorbent polymer.

Specifically, the present invention is a method for recovering pulp fibers from a used absorbent article that includes a water-permeable front sheet, a water-impermeable back sheet and an absorbent body containing pulp fibers and a superabsorbent polymer, wherein the method includes a step in which at least one open hole with a circle equivalent diameter of 5 to 45 mm, or at least one 10- to 45-mm cut is formed in the front sheet and/or back sheet of the used absorbent article, and a step in which the used absorbent article provided with the open hole or cut is agitated in an organic acid aqueous solution with a pH of no higher than 2.5, the superabsorbent polymer is inactivated, and the pulp fibers and superabsorbent polymer are discharged from the used absorbent article through the open hole or cut, to prepare a mixture including the pulp fibers, inactivated superabsorbent polymer, front sheet material, back sheet material and organic acid aqueous solution.

The invention encompasses the following aspects.

[1] A method of recovering pulp fibers from a used absorbent article that includes a water-permeable front sheet, a water-impermeable back sheet and an absorbent body containing pulp fibers and a superabsorbent polymer, wherein the method includes a step in which at least one open hole with a circle equivalent diameter of 5 to 45 mm, or at least one 10- to 45-mm cut, is formed in the front sheet and/or back sheet of the used absorbent article, and a step in which the used absorbent article provided with the open hole or cut is agitated in an organic acid aqueous solution with a pH of no higher than 2.5, the superabsorbent polymer is inactivated, and the pulp fibers and superabsorbent polymer are discharged front the used absorbent article through the open hole or cut, to prepare a mixture including the pulp fibers, inactivated superabsorbent polymer, front sheet material, back sheet material and organic acid aqueous solution.

[2] The method according to [1], which further includes a step in which the mixture is passed through a screen having a mesh opening of 5 to 15 mm, for separation into a mixture containing the pulp fibers, the inactivated superabsorbent polymer and the organic acid aqueous solution, and a mixture containing the front sheet material and the back sheet material.

[3] The method according to [2], which further includes a step of treating the mixture containing the pulp fibers, the inactivated superabsorbent polymer and the organic acid aqueous solution with an oxidizing agent, to decompose, reduce in molecular weight and solubilize the inactivated superabsorbent polymer.

[4] The method according to [3], which further includes a step of separating the pulp fibers from the mixture that has been treated with the oxidizing agent.

[5] The method according to any one of [1] to [4], wherein the organic acid is citric acid.

[6] The method according to [5], wherein the citric acid concentration in the organic acid aqueous solution is 2 mass % or greater.

[7] The method according to any one of [2] to [4], wherein the front sheet or back sheet includes a material composed of a thermoplastic resin, and the method further includes a step in which the mixture containing the front sheet material and the back sheet material is dried, and the material composed of a thermoplastic resin is separated from a dried mixture.

[8] The method according to any one of [2] to [4], wherein the back sheet includes a thermoplastic resin film, and the method further includes a step in which the mixture containing the front sheet material and the back sheet material is dried, and the thermoplastic resin film is separated from a dried mixture.

[9] The method according to any one of [1] to [8], wherein the absorbent article is at least one type selected from the group consisting of paper diapers, urine-absorbing pads, bed sheets, sanitary napkins and pet sheets.

Advantageous Effects of Invention

According to the method of the invention it is possible to easily separate pulp fibers and a superabsorbent polymer from a used absorbent article that includes a water-permeable front sheet, a water-impermeable back sheet and an absorbent body containing pulp fibers and a superabsorbent polymer, and to recover the pulp fibers with minimal damage.

DESCRIPTION OF EMBODIMENTS

The invention is a method for recovering pulp fibers from a used absorbent article that includes a water-permeable front sheet, a water-impermeable back sheet and an absorbent body containing pulp fibers and a superabsorbent polymer.

The absorbent article is not particularly restricted so long as it includes a water-permeable front sheet, a water-impermeable back sheet and an absorbent body containing pulp fibers and a superabsorbent polymer, and examples include paper diapers, urine-absorbing pads, bed sheets, sanitary napkins and pet sheets.

The water-permeable front sheet is not limited so long as it is water-permeable, and it may be a water-permeable nonwoven fabric made of fibers of a thermoplastic resin such as polyethylene, polypropylene or polyester, or a thermoplastic resin film with open holes.

The water-impermeable back sheet is also not limited so long as it is water-impermeable, and it may be a film of a thermoplastic resin such as polyethylene, polypropylene or polyester, or a water-impermeable nonwoven fabric made of fibers of a thermoplastic resin.

The absorbent body contains pulp fibers and a superabsorbent polymer.

The pulp fibers are not particularly restricted, and examples include fluffy pulp fibers and chemical pulp fibers.

A superabsorbent polymer, also known as SAP, has a three-dimensional network structure with an appropriately crosslinked water-soluble polymer, and it therefore absorbs a few hundred to a few thousand times its weight in water while being essentially water-insoluble and preventing absorbed water from emerging even with some degree of pressure application, and examples thereof include acrylic acid-based, starch-based and amino acid-based particulate or fibrous polymers.

The method of the invention includes a step in which the front sheet and/or back sheet of the used absorbent article is provided with at least one open hole having a circle equivalent diameter of 5 to 45 mm, or at least one 10- to 45-min cut (hereunder also referred to simply as "hole-opening step"). By forming an open hole or cut in the front sheet and/or back sheet of the used absorbent article, the pulp fibers and superabsorbent polymer inside the used absorbent article are caused to leak out from the open hole by a water stream produced during agitation in the organic acid aqueous solution in the subsequent step, allowing separation of the pulp and superabsorbent polymer from the nonwoven fabric and film while leaving the form of the used absorbent article.

The shape of the open hole is not particularly restricted and may be circular, elliptical, square, rectangular, triangular or star-shaped, for example. The size of the open hole is 5 to 45 mm, preferably 10 to 40 mm and more preferably 15 to 35 mm, as the circle equivalent diameter. The circle equivalent diameter is the diameter of a circle having the same area as the area of the open hole. When a cut is formed, the shape of the cut is not particularly restricted, and it may be a straight line, curve, cross or x-shape. The length of the cut is 10 to 45 mm, preferably 15 to 40 mm and more preferably 20 to 35 mm. If the circle equivalent diameter of the open hole or the length of the cut is too small, it will not be possible to cause the pulp fibers and superabsorbent polymer inside the used absorbent article to efficiently leak out from the open hole or cut by the water stream produced during agitation in the organic acid aqueous solution in the subsequent step. If the circle equivalent diameter of the open hole or the length of the cut is too large, the water-impermeable back sheet may rupture by impact during agitation, making it impossible to maintain the shape of the diaper, causing it to be finely broken up, and potentially impairing the efficiency during separation and recovery.

The number of open holes or cuts formed in the front sheet and/or back sheet may be one, but it is preferably more than one, and more preferably 5 to 30.

The locations of the open holes or cuts formed in the front sheet and/or back sheet are not limited so long as they allow the pulp fibers and superabsorbent polymer to be discharged from the used absorbent article in the subsequent step, but they are preferably locations where the absorbent body is present.

The method of forming the open holes is not particularly restricted, and for example, they may be formed by loading the used absorbent article into a press perforating device and pressing it with a perforating rod or the like. The method of forming cuts is also not particularly restricted, and for example, they may be formed by using a cutter to cut the front sheet and/or back sheet.

The open holes or cuts may be formed in either the front sheet or the back sheet, or in both. When the open holes or cuts are to be formed only in one of the front sheet or the back sheet they may be formed in either the front sheet or back sheet, but they are preferably formed in the back sheet since the back sheet is usually wrapped on the outer side for discarding when a used diaper is to be disposed of.

The method of the invention includes a step in which a used absorbent article provided with an open hole or cut is agitated in an organic acid aqueous solution with a pH of no higher than 2.5, and the superabsorbent polymer is inactivated while the pulp fibers and superabsorbent polymer are discharged from the used absorbent article through the open hole or cut, to prepare a mixture including the pulp fibers, the inactivated superabsorbent polymer, the front sheet material, the back sheet material and the organic acid aqueous solution (hereunder also referred to simply as "organic acid treatment step"). By treatment with an organic acid aqueous solution having a pH of no higher than 2.5, the Na ions of the superabsorbent polymer in the used absorbent article are replaced by H ions, allowing the water-absorbing capacity of the superabsorbent polymer to be notably reduced, and helping to prevent water-swelled expansion of the superabsorbent polymer during treatment which leads to reduced treatment efficiency. By forming an open hole or cut in the used absorbent article in advance, agitation in an aqueous solution will cause the pulp fibers and inactivated superabsorbent, polymer in the used absorbent article to gradually exit through the open hole or cut into the treatment tank. When the organic acid treatment step is complete, most of the pulp fibers and inactivated superabsorbent polymer in the absorbent article will have exited into the treatment tank, with the absorbent article essentially maintaining its original form, thus allowing separation of the nonwoven fabric and film.

Organic acids include citric acid, tartaric acid, glycolic acid, malic acid, succinic acid, acetic acid and ascorbic acid, with citric acid being particularly preferred. The chelating effect of citric acid traps metal ions and the like present in excreta, allowing their removal, and the washing effect of citric acid can potentially provide a high fouling component-removal effect.

The pH of the organic acid aqueous solution is no higher than 2.5, preferably 1.3 to 2.4 and more preferably 1.5 to 2.1. If the pH is too high, it may not be possible to sufficiently lower the water-absorbing capacity of the superabsorbent polymer. In addition, the primary sterilizing ability may be reduced and the microbicidal rate may be reduced. If the pH is too low, the risk of corrosion of the equipment will increase, lowering its service life, and large amounts of alkaline chemicals may be necessary for neutralizing treatment during waste water treatment.

The organic acid concentration of the organic acid aqueous solution is not restricted so long as the pH of the organic acid aqueous solution is no higher than 2.5, but when the organic acid is citric acid, the citric acid concentration is preferably 2 mass % or greater, more preferably 2.0 to 4.0 mass % and even more preferably 2.0 to 3.0 mass %.

The organic acid aqueous solution may also contain a detergent or the like.

The treatment temperature, i.e. the organic acid aqueous solution temperature, is not particularly restricted, and it may be heated or at room temperature, such as at 15 to 30° C.

The treatment time is not limited so long as the superabsorbent polymer can be inactivated and most of the pulp fibers and superabsorbent polymer can be discharged from the used absorbent article, but it is preferably 5 to 60 minutes and more preferably 10 to 30 minutes.

The amount of organic acid aqueous solution is not limited so long as the superabsorbent polymer can be inactivated and most of the pulp fibers and superabsorbent polymer can be discharged from the used absorbent article, but it is preferably 300 to 3000 parts by mass, more preferably 500 to 2500 parts by mass and even more preferably 1000 to 2000 parts by mass with respect to 100 parts by mass of the used absorbent article.

The specific method for carrying out the organic acid treatment step is not particularly restricted, and for example, a prescribed amount of the used absorbent article is loaded into washing equipment, after which an organic acid aqueous solution with a pH of no higher than 2.5 is loaded in and the mixture is agitated. A detergent or the like may also be added to the organic acid aqueous solution if necessary.

The method of the invention may further include a step in which the mixture including the pulp fibers, inactivated superabsorbent polymer, front sheet material, back sheet material and organic acid aqueous solution, obtained by the organic acid treatment step, is passed through a screen with a mesh opening of 5 to 15 mm for separation into a mixture containing the pulp fibers, the inactivated superabsorbent polymer and the organic acid aqueous solution, and a mixture containing the front sheet material and the back sheet material (hereunder also referred to as "first separating step"). In this step, the mixture containing the pulp fibers, the inactivated superabsorbent polymer and the organic acid aqueous solution passes through the screen while the mixture containing the front sheet material and the back sheet material remains on the screen, thus allowing the two to be separated. The mesh opening of the screen may be 5 to 15 mm, but is preferably 7 to 13 mm. If the mesh opening of the screen is in this range, the back sheet will be separable even if a portion therefore becomes ruptured.

The method of the invention may further include a step in which the mixture containing the pulp fibers, the inactivated superabsorbent polymer and the organic acid aqueous solution is treated with an oxidizing agent to decompose, reduce in molecular weight and solubilize the inactivated superabsorbent polymer (hereunder also referred to simply as "oxidizing agent treatment step"). By treating the mixture containing the pulp fibers, the inactivated superabsorbent polymer and the organic acid aqueous solution with an oxidizing agent, it is possible to oxidatively decompose, reduce in molecular weight and solubilize the inactivated superabsorbent polymer while carrying out secondary sterilization, bleaching and deodorization of the pulp fibers. The decomposed, molecular weight-reduced and solubilized state of the superabsorbent polymer means a state in which it passes through a screen with a 2 mm mesh opening. In other words, in this step, the superabsorbent polymer is decomposed until it passes through a screen with a mesh opening of 2 mm.

The oxidizing agent is not limited so long as it can decompose, reduce in molecular weight and solubilize the inactivated superabsorbent polymer, and examples include chlorine dioxide, ozone and sodium hypochlorite. Ozone is preferred among these from the viewpoint of high decomposing power and effect on the environment.

The method of treatment with the oxidizing agent is not limited so long as it can decompose, reduce in molecular weight and solubilize the inactivated superabsorbent polymer, and for example, the oxidizing agent may be added to the mixture containing the pulp fibers, the inactivated superabsorbent polymer and the organic acid aqueous solution, which is obtained after separation through the screen in the first separating step. Alternatively, the mixture may be further passed through a fine screen that does not allow passage of the pulp fibers and inactivated superabsorbent polymer, thus separating the pulp fibers and inactivated superabsorbent polymer from the mixture, and the separated pulp fibers and inactivated superabsorbent polymer may be added to an aqueous solution of the oxidizing agent.

When ozone is used as the oxidizing agent, the oxidizing agent treatment may be carried out by contacting the mixture containing the pulp fibers and inactivated superabsorbent polymer with the ozone, or more specifically, the ozone may be blown into the mixture containing the pulp fibers, the inactivated superabsorbent polymer and the organic acid aqueous solution. Ozone can be generated using, for example, an ozone water generator (such as an ED-OWX-2 ozone water exposure tester by EcoDesign, Inc. or an OS-25V ozone generator by Mitsubishi Electric Corp.).

When ozone is to be blown into the mixture containing the pulp fibers, the inactivated superabsorbent polymer and the organic acid aqueous solution, the ozone concentration in the mixture is not particularly restricted so long as it is a concentration allowing decomposition of the superabsorbent polymer, and it is preferably 1 to 50 ppm by mass, more preferably 2 to 40 ppm by mass and even more preferably 3 to 30 ppm by mass. If the concentration is too low it may not be possible to completely solubilize the superabsorbent polymer, potentially leading to residue of the superabsorbent polymer in the recovered pulp fibers, or sterilization may be inadequate. If the concentration is too high, conversely, the oxidizing power will increase, potentially damaging the pulp fibers and possibly causing problems in terms of safety.

The ozone treatment time is not particularly restricted so long as it is a time allowing the superabsorbent polymer to be decomposed. The treatment time may be short if the ozone concentration is high, but it must be a longer time if the ozone concentration is low.

The product of the ozone concentration (ppm) and the treatment time (min) (hereunder also referred to as "CT value") is preferably 100 to 6000 ppm·min, more preferably 200 to 4800 ppm min and even more preferably 300 to 3600 ppm·min. If the CT value is too low it may not be possible to completely solubilize the superabsorbent polymer, potentially leading to residue of the superabsorbent polymer in the recovered pulp fibers. Conversely, an excessively large CT value may result in damage to the pulp fibers, reduced safety and increased manufacturing cost.

The treatment time will depend on the ozone concentration, as explained above, but it is preferably 20 to 120 minutes, more preferably 30 to 100 minutes and even more preferably 40 to 80 minutes.

The temperature during ozone treatment is not particularly restricted so long as it is a temperature allowing the superabsorbent polymer to be decomposed. When ozone is to be blown into the mixture containing the pulp fibers, the inactivated superabsorbent polymer and the organic acid aqueous solution, the mixture may be heated or it may be at room temperature.

In the oxidizing agent treatment step, the superabsorbent polymer undergoes oxidative decomposition by the oxidizing agent and the three-dimensional network structure of the superabsorbent polymer collapses, the superabsorbent polymer losing its water retention and becoming reduced in molecular weight and solubilized.

When ozone is to be blown into the mixture containing the pulp fibers, the inactivated superabsorbent polymer and the organic acid aqueous solution, the mixture is preferably acidic. More preferably, the pH of the mixture is no higher than 2.5 and even more preferably 1.5 to 2.4. Treatment in an acidic state can improve the superabsorbent polymer decomposing and removal effect of the ozone, allowing the superabsorbent polymer to be decomposed in a shorter dine.

When chlorine dioxide is used as the oxidizing agent, the oxidizing agent treatment may be carried out by contacting the mixture containing the pulp fibers and inactivated superabsorbent polymer with the chlorine dioxide, or more specifically, the chlorine dioxide may be blown into the mixture containing the pulp fibers, the inactivated superabsorbent polymer and the organic acid aqueous solution. The chlorine dioxide used may be a commercially available product.

When chlorine dioxide is to be blown into the mixture containing the pulp fibers, the inactivated superabsorbent polymer and the organic acid aqueous solution, the chlorine dioxide concentration in the mixture is not particularly restricted so long as it is a concentration allowing decomposition of the superabsorbent polymer, and it is preferably 150 to 1100 ppm by mass, more preferably 200 to 1000 ppm by mass and even more preferably 300 to 900 ppm by mass. If the concentration is too low it may not be possible to completely solubilize the superabsorbent polymer, potentially leading to residue of the superabsorbent polymer in the recovered pulp fibers, or sterilization may be inadequate. If the concentration is too high, conversely, the oxidizing power will increase, potentially damaging the pulp fibers and possibly causing problems in terms of safety.

The treatment time is the same as for ozone treatment

When sodium hypochlorite is used as the oxidizing agent, the oxidizing agent treatment may be carried out by contacting the mixture containing the pulp fibers and inactivated superabsorbent polymer with the sodium hypochlorite, or more specifically, the sodium hypochlorite may be added to the mixture containing the pulp fibers, the inactivated superabsorbent polymer and the organic acid aqueous solution, or the pulp fibers and inactivated superabsorbent polymer separated from the mixture by a screen may be immersed in an aqueous solution of the sodium hypochlorite. The sodium hypochlorite used may be a commercially available product.

When sodium hypochlorite is to be added to the mixture containing the pulp fibers, the inactivated superabsorbent polymer and the organic acid aqueous solution, or when the pulp fibers and inactivated superabsorbent polymer are to be immersed in an aqueous solution of the sodium hypochlorite, the sodium hypochlorite concentration in the mixture or in the aqueous solution of the sodium hypochlorite is not particularly restricted so long as it is a concentration allowing decomposition of the superabsorbent polymer, but it is preferably 0.5 to 2 mass % and more preferably 0.75 to 1.5 mass %. If the concentration is too low it may not be possible to completely solubilize the superabsorbent polymer, potentially leading to residue of the superabsorbent polymer in the recovered pulp fibers, or sterilization may be inadequate. If the concentration is too high, conversely, the oxidizing power will increase, potentially damaging the pulp fibers and possibly causing problems in terms of safety. Incidentally, for complete sterilizing treatment of spores (*Bacillus subtilis* and the like), the sodium hypochlorite concentration is preferably 1.0 mass % or greater.

The treatment time is the same as for ozone treatment.

The method of the invention may further include a step of separating the pulp fibers from a mixture treated by an oxidizing agent (hereunder also referred to simply as "pulp fiber separating step"). The method of separating the pulp fibers is not particularly restricted, and for example, the pulp fibers may be separated by passing the mixture that has been treated by the oxidizing agent through a screen with a mesh opening of 0.15 to 2.0 mm. If the mixture that has been treated by the oxidizing agent, and more specifically the aqueous solution containing the pulp fibers and decomposed superabsorbent polymer, is passed through a screen with a mesh opening of 0.15 to 2.0 mm, the aqueous solution containing the decomposed superabsorbent polymer will pass through the screen while the pulp fibers will remain on the screen.

The separated pulp fibers may be dewatered, dried and recovered as necessary.

The drying temperature for drying is preferably 105 to 210° C., more preferably 110 to 1.90° C. and even more preferably 120 to 180° C. The drying time will depend on the drying temperature, but it is preferably 10 to 120 minutes, more preferably 15 to 100 minutes and even more preferably 20 to 90 minutes.

When the front sheet or back sheet includes a material composed of a thermoplastic resin, the method of the invention may further include a step in which the mixture containing the front sheet material and the back sheet material obtained by the first separating step is dried and the material composed of a thermoplastic resin is separated from the dried mixture (hereunder also referred to simply as "thermoplastic resin material separating step"). By drying the mixture containing the front sheet material and the back sheet material, it is possible to carry out secondary sterilization of the mixture containing the front sheet material and the back sheet material. The "material composed of a thermoplastic resin" referred to here is a nonwoven fabric composed of fibers of a thermoplastic resin such as polyethylene, polypropylene or polyester, or a film of a thermoplastic resin. The separated material composed of a thermoplastic resin may be converted to RPF (conversion to solid fuel). When an oxidizing agent treatment step is not provided, or when an oxidizing agent treatment step is provided but ozone is used as the oxidizing agent, no chlorine-based agents will be present during the RPF conversion step, and therefore high-quality RPF can be produced without damaging the furnace.

When the back sheet includes a thermoplastic resin film, the method of the invention may further include a step in which the mixture containing the front sheet material and the back sheet material is dried and the thermoplastic resin film is separated from the dried mixture (hereunder also referred to simply as "film separating step"). By drying the mixture containing the front sheet material and the back sheet material, it is possible to carry out secondary sterilization of the mixture containing the front sheet material and the back sheet material. Since the front sheet and back sheet of the used absorbent article remain essentially in their original forms both after the organic acid treatment step and after the first separating step, the thermoplastic resin film can be easily detached, separated and recovered. The separated thermoplastic resin film may be pelletized for regeneration as a plastic bag or film. The remaining portion left after separating the thermoplastic resin film from the mixture containing the front sheet material and the back sheet material will consist mainly of the material composed of a thermoplastic resin, and it can therefore be sent onward for RPF conversion (conversion to solid fuel).

When lime is to be used for treatment of the used absorbent article as described in Japanese Unexamined Patent Publication No. 2010-84031, the lime creates an environment with a high pH (12.4) inside the treatment tank, and the cellulose swells causing the pulp fibers to undergo alkali cellulose conversion and degradation, but since the present invention uses an organic acid with a pH of no higher than 2.5 for inactivation of the superabsorbent polymer, the pulp fibers are less likely to undergo degradation, while the open holes or cuts provided in the used absorbent article cause the pulp fibers and superabsorbent polymer inside the used absorbent article to leak out from the open holes or cuts by a water stream produced during agitation in the organic acid treatment step, allowing separation of the pulp fibers and superabsorbent polymer from the nonwoven fabric and film while leaving the form of the used absorbent article. When citric acid is used as the organic acid, the chelating effect and washing power of the citric acid can potentially provide an effect of removing fouling components from excreta. A sterilizing effect and a deodorant effect against alkaline odors may also be expected.

By decomposing and removing the inactivated superabsorbent polymer with an oxidizing agent, it is possible to prevent contamination of the recovered pulp fibers or drastic increase in sludge due to water absorption by the superabsorbent polymer. By adjusting the type and concentration of oxidizing agent used, it is possible to simultaneously carry out oxidative decomposition and sterilization of the inactivated superabsorbent polymer.

When an oxidizing agent treatment step is not provided, or when an oxidizing agent treatment step is provided but ozone is used as the oxidizing agent, since absolutely no chlorine-based agents are used in the step of recovering the nonwoven fabric and film materials, high-quality RPF can be produced, which is unlikely to damage the combustion furnace. If the film material is separated and recovered, it can be reused as a raw material for a bag or film. The form of the used absorbent article is maintained even after the organic acid treatment, and the film material can be easily detached from the used absorbent article and efficiently recovered.

Since no salts are used during the treatment steps, there is no residue of salts in the recovered pulp fibers, and high quality pulp with a low ash content can be recovered.

According to the method of the invention, degradation of pulp fibers can be minimized even when pulp fibers are regenerated from a used absorbent article, and it is possible to minimize reduction in quality even with repeated regeneration. Increase in the ash content of the pulp fibers and reduction in absorption performance are also less likely to result, compared to the prior art.

Spore forming bacteria (*Bacillus subtilis*, *Bacillus cereus*, etc.) can also be sterilized, and safe pulp fibers with low impurities can be recovered due to a high washing effect and metal ion-removal effect.

The acidic effect of the organic acid accelerates replacement of Na ions in the superabsorbent polymer with H ions, and when the superabsorbent polymer is sodium polyacrylate-based, the sodium polyacrylate is converted to polyacrylic acid, lowering the water-absorbing capacity of the superabsorbent polymer and thereby reducing absorption of the organic acid aqueous solution during washing, to allow treatment to be carried out with a smaller amount of solution. Furthermore, water-absorbing gel becomes smaller, and as a result of screen separation after completion of washing, most of it is discharged along with the pulp fibers out of the treatment tank together with the treatment drainage, and thereafter most of the residue in the tank consists of non-water-absorbing materials such as the nonwoven fabric and film, thus increasing the drying efficiency.

Since the inactivated superabsorbent polymer that has been discharged out of the treatment tank along with the pulp fibers is oxidatively decomposed and reduced in molecular weight by the oxidizing agent, it can be easily treated by ordinary waste water treatment. Decomposition and removal of the inactivated superabsorbent polymer can reduce impurities in the pulp fibers. Moreover, the effect of the oxidizing agent may also be expected to have a sterilizing, bleaching and deodorizing effect on the pulp fibers.

The form of the used absorbent article is maintained even after the organic acid treatment, and thermoplastic resin film material can be easily detached from the absorbent article and efficiently recovered.

By forming open holes or cuts in the used absorbent article before organic acid treatment, it is possible to cause the pulp fibers and superabsorbent polymer inside the absorbent article to leak out during the organic acid treatment and be efficiently separated and recovered, while maintaining the shape of the absorbent article.

EXAMPLES

The present invention will now be explained in more specific detail through the following examples, with the understanding that the invention is in no way limited to the examples.

Example 1

After immersing 100 g of standard compost (YK-8, product of Yawata Corp.) in 1 L of ion-exchanged water and stirring for 5 minutes, the mixture was allowed to stand for 30 minutes and 240 mL of the supernatant solution was sampled, to prepare artificial sewage. The prepared artificial sewage was subjected to ATP inspection using a Lumitester PD-30 by Kikkoman Corp. as the measuring instrument, resulting in an ATP value of 16126.

After using commercially available paper diapers (Moony$^R$ M size, by Unicharm Corp.) to absorb 240 mL of the previously prepared artificial sewage, a 5 mm punch by Ichinen Mitsutomo Co., Ltd. was used to perforate 24 circular holes with 5 mm diameters in the back sheets. One of the perforated paper diapers was loaded into a washing tank of a dual-tank miniature washing machine ("HareBare" AST-01 by Alumis Co.), and then 10 L of an aqueous solution comprising citric acid (product of Fuso Chemical Co., Ltd.) dissolved at a concentration of 2 mass % (pH 2.1) was loaded in and washing was carried out for 15 minutes at room temperature, after which a strainer with a hole size of φ10 mm was used to sift out the large-sized solids such as the nonwoven fabric and film that were floating in the liquid inside the washing tank, they were drained, and the pulp fibers and inactivated superabsorbent polymer remaining in the tank, as well as the pulp fibers and inactivated superabsorbent polymer that had been discharged out of the tank together with the drainage, were recovered and subjected to ATP inspection. The results of the ATP inspection yielded an ATP value of 0.

Next, the pulp fibers and inactivated superabsorbent polymer were placed in a nylon net (250 mesh nylon net by NBC Meshtec, Inc.) bag (250 mm×250 mm), and dewatered for 5 minutes in a dewatering tank. The dewatered pulp fibers and superabsorbent polymer were immersed in a 1 mass % sodium hypochlorite aqueous solution together with the nylon net bag and subjected to stirring and washing for 5 minutes, and after again dewatering for 5 minutes in a dewatering tank, they were dried for 24 hours with a hot air drier at 1.05° C., and then the pulp fibers were recovered. Upon analyzing the ash content, water absorption factor and water retention factor of the recovered pulp fibers, the ash content was 0.44 mass %, the water absorption factor was 16.0 g/g and the water retention factor was 7.1 g/g.

Example 2

After immersing 100 g of standard compost (YK-8, product of Yawata Corp.) in 1 L of ion-exchanged water and stirring for 5 minutes, the mixture was allowed to stand for 30 minutes and 240 mL of the supernatant solution was sampled, to prepare artificial sewage. The prepared artificial sewage was subjected to ATP inspection using a Lumitester PD-30 by Kikkoman Corp. as the measuring instrument, resulting in an ATP value of 16126.

After using commercially available paper diapers (Moony$^R$ NI size, by Unicharm Corp.) to absorb 240 mL of the previously prepared artificial sewage, a Universal L-Cutter by Olfa Corp. was used to cut 12 cross-shaped notches with 40 mm-long lines in the back sheet. One of the notched paper diapers was loaded into a washing tank of a dual-tank miniature washing machine ("FlareBare" AST-01 by Alumis Co.), and then 10 L of an aqueous solution comprising citric acid (product of Fuso Chemical Co., Ltd.) dissolved at a concentration of 2 mass % (pH 2.1) was loaded in and washing was carried out for 15 minutes at room temperature, after which a strainer with a hole size of φ10 mm was used to sift out the large-sized solids such as the nonwoven fabric and film that were floating in the liquid inside the washing tank, they were drained, and the pulp fibers and inactivated superabsorbent polymer remaining in the tank, as well as the pulp fibers and inactivated superabsorbent polymer that had been discharged out of the tank together with the drainage, were recovered and subjected to ATP inspection. The results of the ATP inspection yielded an ATP value of 0.

Next, the pulp fibers and inactivated superabsorbent polymer were placed in a nylon net (250 mesh nylon net by NBC Meshtec, Inc.) bag (250 mm×250 mm), and dewatered for 5 minutes in a dewatering tank. The dewatered pulp fibers and superabsorbent polymer were immersed in a 1 mass % sodium hypochlorite aqueous solution together with the mesh bag and subjected to stirring and washing for 5 minutes, and after again dewatering for 5 minutes in a dewatering tank, they were dried for 24 hours with a hot air drier at 105° C., and then the pulp fibers were recovered. Upon analyzing the ash content, water absorption factor and water retention factor of the recovered pulp fibers, the ash content was 0.40 mass %, the water absorption factor was 16.5 g/g and the water retention factor was 7.5 g/g.

Comparative Example 1

A test was conducted by the method described in Japanese Unexamined Patent Publication No. 2010-84031. Specifically, after using commercially available paper diapers (Moony$^R$ M size, by Unicharm Corp.) to absorb 240 mL of the previously prepared artificial sewage, one paper diaper was loaded into a washing tank of a dual-tank miniature washing machine ("HareBare" AST-01 by Alumis Co.), 80 g of CaO (product of Wako Pure Chemical Industries, Ltd.) was further loaded into the washing tank, and then 6.5 L of 250 ppm sodium hypochlorite (prepared by dilution of a product purchased from Wako Pure Chemical Industries, Ltd.) was loaded in. After 15 minutes of washing, the paper diaper floating in the liquid inside the washing tank was recovered, and since the paper diaper had retained its form without separation, the surface material was physically torn by hand to recover the pulp fibers including the inactivated SAP inside the paper diaper. Upon analyzing the ash content, water absorption factor and water retention factor of the recovered pulp fibers, the ash content was 15.9 mass %, the water absorption factor was 8.0 g/g and the water retention factor was 2.8 g/g.

Example 3

(Verifying Decomposition of Inactivated Superabsorbent Polymer by Oxidizing Agent)

After placing 10 g of inactivated superabsorbent polymer into a nylon net (250 mesh nylon net by NBC Meshtec, Inc.) bag (250 mm×250 mm), and measuring the total mass of the inactivated superabsorbent polymer and the nylon net bag, they were immersed for 60 minutes in 500 g of a sodium hypochlorite aqueous solution with a sodium hypochlorite concentration of 1 mass % at room temperature. When the total mass of the inactivated superabsorbent polymer and the nylon net bag was measured after immersion, the mass was found to be that of the nylon net bag alone. In other words, the inactivated superabsorbent polymer had decomposed, completely eluting from the nylon net (250 mesh nylon net by NBC Meshtec, Inc.).

The methods of analyzing each of the analyzed parameters are as follows.

[Method of Analyzing Pulp Fiber Ash Content]

The ash content is the amount of inorganic substances or nonflammable residue remaining after the organic substances have been ashed. The ash content is measured according to the Sanitary Product Material Standards, "2. General test methods", "5. Ash content test method". Specifically, the ash content is measured in the following manner.

A platinum, quartz or magnetic crucible is strongly preheated at 500 to 550° C. for 1 hour, and after standing to cool, the mass is precisely measured. After taking 2 to 4 g of sample and placing it in the crucible, the mass is precisely measured, removing or displacing the cover of the crucible if necessary, and gentle heating is performed first, followed by gradual increase in the temperature to strong heating at 500 to 550° C. for 4 hours or longer, ashing it until no more carbides remain. After being allowed to cool, the mass is precisely measured. The residue is again ached until reaching a constant mass, and after cooling, the mass is precisely measured and recorded as the ash content (mass %).

[Method of Analyzing Pulp Fiber Water Absorption Factor]

The water absorption factor is the mass of water absorbed by the pulp fibers per unit mass. The water absorption factor is measured in the following manner.

(1) A bag (200 mm×200 mm) of a nylon net (250 mesh nylon net by NBC Mesh tee, s prepared, and its mass $N_0$ (g) is measured.

(2) Approximately 5 g of measuring sample is placed in the nylon net, and the mass $A_0$ (g) including that of the nylon net bag is measured.

(3) After placing 1 L of 0.9% physiological saline in a beaker, the prepared sample-containing nylon net bag is immersed therein and allowed to stand for 3 minutes.

(4) The bag is raised out and allowed to stand for 3 minutes on a draining net for drainage.

(5) The mass A (g) after drainage of the nylon net bag containing the sample is measured.

(6) Another set of nylon nets cut out to the same size is prepared, (3) and (4) are carried out in the same manner but without placing the sample in them, and the mass N (g) of the nylon net bags alone after drainage is measured.

(7) The water absorption factor (times) is calculated by the following formula.

$$\text{Water absorption factor} = (A - N - (A_0 - N_0))/(A_0 - N_0)$$

(8) The measurement is conducted 10 times, and the average value of the 1.0 measurements is recorded.

[Method of Analyzing Pulp Fiber Water Retention Factor]

(9) After completing the measurement of (5) in "Method of analyzing pulp fiber water absorption factor", it is dewatered at 150 G for 90 seconds and the mass D (g) is measured.

(10) Another set of nylon nets cut out to the same size is prepared, (3), (4) and (9) are carried out in the same manner but without placing the sample in them, and the mass N' (g) of the nylon net bags alone after drainage is measured.

(11) The water retention factor (times) is calculated by the following formula.

$$\text{Water retention factor} = N' - (A_0 - N_0))/(A_0 - N_0)$$

INDUSTRIAL APPLICABILITY

The method of the invention can be suitably used to recover pulp fibers from a used absorbent article that includes a water-permeable front sheet, a water-impermeable back she and art absorbent body containing pulp fibers and a superabsorbent polymer.

The invention claimed is:

1. A method of recovering pulp fibers from a used absorbent article that includes a water-permeable front sheet, a water-impermeable back sheet and an absorbent body containing pulp fibers and a superabsorbent polymer, wherein the method includes a step in which at least one open hole with a circle equivalent diameter of 5 to 45 mm, or at least one 10- to 45-mm cut, is formed in the front sheet and/or back sheet of the used absorbent article, and a step in which the used absorbent article provided with the open hole or cut is agitated in an organic acid aqueous solution with a pH of no higher than 2.5, the superabsorbent polymer is inactivated, and the pulp fibers and superabsorbent polymer are discharged from the used absorbent article through the open hole or cut, to prepare a mixture including the pulp fibers, inactivated superabsorbent polymer, front sheet material, back sheet material and organic acid aqueous solution.

2. The method according to claim 1, which further includes a step in which the mixture is passed through a screen having a mesh opening of 5 to 15 mm, for separation into a mixture containing the pulp fibers, the inactivated superabsorbent polymer and the organic acid aqueous solution, and a mixture containing the front sheet material and the back sheet material.

3. The method according to claim 2, which further includes a step of treating the mixture containing the pulp fibers, the inactivated superabsorbent polymer and the organic acid aqueous solution with an oxidizing agent, to decompose, reduce in molecular weight and solubilize the inactivated superabsorbent polymer.

4. The method according to claim 3, which further includes a step of separating the pulp fibers from the mixture that has been treated with the oxidizing agent.

5. The method according to claim 1, wherein the organic acid is citric acid.

6. The method according to claim 5, wherein a citric acid concentration in the organic acid aqueous solution is 2 mass % or greater.

7. The method according to claim 2, wherein the front sheet or back sheet includes a material composed of a thermoplastic resin, and the method further includes a step in which the mixture containing the front sheet material and the back sheet material is dried, and the material composed of a thermoplastic resin is separated from a dried mixture.

8. The method according to claim 2, wherein the back sheet includes a thermoplastic resin film, and the method further includes a step in which the mixture containing the front sheet material and the back sheet material is dried, and the thermoplastic resin film is separated from a dried mixture.

9. The method according to claim 1, wherein the absorbent article is at least one type selected from the group consisting of paper diapers, urine-absorbing pads, bed sheets, sanitary napkins and pet sheets.

* * * * *